United States Patent
Ward

[11] Patent Number: 5,984,893
[45] Date of Patent: Nov. 16, 1999

[54] BLOOD INFUSION CONTROL SYSTEM

[76] Inventor: Roger T. Ward, 4830 Elmwood Ave., Unit 302, Los Angeles, Calif. 90004

[21] Appl. No.: 09/049,414

[22] Filed: Mar. 27, 1998

Related U.S. Application Data

[60] Provisional application No. 60/042,049, Mar. 27, 1997.

[51] Int. Cl.$^6$ .................................................. A61M 5/142
[52] U.S. Cl. ............................. 604/131; 128/DIG. 12; 128/DIG. 13
[58] Field of Search .................................. 604/131, 141, 604/151, 152; 128/DIG. 12, DIG. 13

[56] References Cited

U.S. PATENT DOCUMENTS

| | | | |
|---|---|---|---|
| 3,949,746 | 4/1976 | Wallack | 604/152 |
| 4,464,170 | 8/1984 | Ciemens et al. | 128/DIG. 13 |
| 4,705,508 | 11/1987 | Karnavas et al. | |
| 4,747,826 | 5/1988 | Sassano | 604/151 |
| 4,769,001 | 9/1988 | Prince | 128/DIG. 13 |
| 4,842,576 | 6/1989 | Lysacht et al. | 604/131 |
| 4,871,351 | 10/1989 | Feingold | 604/131 |
| 4,874,359 | 10/1989 | White et al. | 128/DIG. 13 |
| 4,888,004 | 12/1989 | Williamson, IV et al. | 604/151 |
| 4,966,579 | 10/1990 | Polaschegg | 604/131 |
| 5,002,055 | 3/1991 | Merki et al. | 128/DIG. 12 |
| 5,061,241 | 10/1991 | Stephens, Jr. et al. | |
| 5,378,231 | 1/1995 | Johnson et al. | 604/151 |
| 5,385,539 | 1/1995 | Maynard | |
| 5,385,540 | 1/1995 | Abbott et al. | 604/151 |
| 5,423,747 | 6/1995 | Amano | 604/151 |
| 5,547,470 | 8/1996 | Johnson et al. | 604/151 |
| 5,573,502 | 11/1996 | Le Cocq et al. | 604/151 |
| 5,573,505 | 11/1996 | Johnson et al. | 604/131 |

*Primary Examiner*—Paul J. Hirsch
*Attorney, Agent, or Firm*—Loeb & Loeb LLP

[57] ABSTRACT

The Blood Infusion Control System of the present invention integrates components of rapid infusion systems with a computer controller designed to synchronize two infusion pumps in a manner that produces a pre-selected patient hematocrit (HCT*) while reporting the patient's estimated blood volume ($BV_E$). In order to attain HCT*, the Blood Replacement Controller (BRC) drives a dual-pump assembly to deliver streams of asanguinous fluid and blood through flexible conduits into intravenous (IV) catheters to mix with the patient's blood volume having an initial hematocrit ($HCT_i$). The BRC utilizes measured patient data as feedback input to control flowrates of the two-pump infusion assembly. The patient's estimated blood volume is extrapolated from hematocrit changes in response to the fluid and blood infusion. The major components that comprise BICS are two infusion pumps, a microcomputer controller to actuate the two pumps, a heat exchanger, a bubble trap-filter, air/temperature/pressure sensors, and disposable tubing conduits. The design methodology represents a blood infusion device that can rapidly deliver filtered, bubble free, warmed volumes to patients with significant hypovolemia. This subject invention is a sample data control system that rapidly dispenses crystalloid/colloid fluids and red blood cells by venous infusion in a manner that 1) achieves HCT* in the patient and 2) reports the patient's $BV_E$. BICS could enhance the ability of clinical teams in operating rooms and trauma receiving areas to stabilize patients suffering cardiovascular deterioration from acute blood loss.

20 Claims, 11 Drawing Sheets

IDEALIZED TIME PROFILES GIVING FLOWRATES FOR
RBC AND FLUID THAT WILL ELEVATE A PATIENT'S
HEMATOCRIT FROM $HCT_E = 25\%$ TO $HCT^* = 30\%$

INITIAL MEASURED $HCT_E = 25\%$

OPERATOR SETS:   TF = RBC + FLUID = 100 ml/min ;   $HCT^* = 30\%$

HEMATOCRIT VALUES THAT RESULT FROM
THE PUMP FLOWRATES GIVEN ABOVE

IDEALIZED TIME PROFILES GIVING FLOWRATES FOR RBC AND FLUID THAT WILL DROP A PATIENT'S HEMATOCRIT FROM $HCT_E = 30\%$ TO $HCT^* = 25\%$

INITIAL MEASURED $HCT_E$ = 30%

OPERATOR SETS:   TF = RBC + FLUID = 100 ml/min ;   $HCT^*$ = 25%

HEMATOCRIT VALUES THAT RESULT FROM THE PUMP FLOWRATES GIVEN ABOVE

BLOOD INFUSION CONTROL SYSTEM

RELATED APPLICATION

This Application claims priority of Provisional Patent Application No. 60/042,049, filed Mar. 27, 1997, incorporated by reference herein.

BACKGROUND OF THE INVENTION

1. Field of the Invention

The present invention relates to fluid infusion systems in general, and specifically to a rapid, venous infusion system which controls the percentage of the volume of a patient's intravascular blood space occupied by red blood cells known as the "hematocrit" and empirically monitors a patient's estimated blood volume by using physiological inputs provided manually by the operator or automatically by sensors.

2. Description of the Related Art

Every acutely-ill patient who has a depleted blood volume from trauma or other disease process will require infusion of intravenous (IV) fluids to help correct the resulting cardiovascular deterioration. When large volumes of IV fluids are needed to stabilize the circulatory system, a point is reached when transfusion with a red blood cell (RBC) source is required in order to prevent extreme hemodilution (reduction in concentration of RBC) in the patient. Transfused blood is a suspension composed of red blood cells, having a source hematocrit given by $HCT_S$ with the remainder consisting of plasma protein colloids and water.

Many types of surgery such as major vascular repair, orthopedic surgery, organ transplant, and trauma create transfusion needs related to continued replacement of an ongoing blood loss. The decisions of 1) when to transfuse blood and 2) how much blood to transfuse is usually based on factors such as the most recent hematocrit (HCT) value of the patient, size of the patient, and amount of crystalloid or colloid fluids needed to be administered. The timing and rate at which to infuse blood into a patient is often based on an "empirical" judgment of the attending medical staff. Such a trial-and-error approach frequently results in substantial variability of patient hematocrit (HCT) values because blood is traditionally transfused in a unit by unit manner when the hematocrit HCT falls below a "transfusion trigger". In massively transfused patients, it is important to maintain blood volume by blending packed red blood cells and dilution fluids in the proper proportion for regulation of the hematocrit (HCT).

Several methods are disclosed in the prior art to estimate a patient's blood volume using kilogram body weight or body surface area. Methods have recently been described to estimate a patient's blood volume using intravenously injected dilution markers. Computational models used to guide fluid administration during expansion of a patient's blood volume assumes that 1) approximately 30% of isotonic crystalloids infused will remain within the intravascular compartment, and 2) approximately 100% of colloids infused will remain within the intravascular compartment during an initial 30 minute time period. Approximately 25–30% of urine output comes from the plasma volume based on urine osmolarity.

Examples of apparatus and components for rapid fluid infusion have been described in U.S. Pat. Nos. 3,731,679; 3,990,444; 4,138;288; 4,178,927; 4,210,138; 4,217,993; 4,256,437; 4,705,508; 4,747,826; 4,874,359; 5,061,241; 5,385,539; 5,423,747; and 5,573,502. These devices employ a single infusion pump (usually a roller pump) to dispense fluid/blood mixtures from a cardiotomy reservoir through a heat exchanger and air trap and then to the patient. Regulation of a patient's hematocrit (HCT) is attempted by the operator who must add fluid or units of blood to the mixing chamber in a schedule that properly modulates the composition of the infusion delivered via the single pump. These one-pump infusion systems can be wasteful of a critical donor blood supply because extra units of blood are needed to "prime" the mixing reservoir. A blood infusion device which will achieve a pre-selected hematocrit (HCT) in the patient as large or small volumes of physiologic fluids and blood are rapidly administered to patients represents an advantage.

No blood infusion device now exists which can rapidly deliver liters of physiologic fluid and blood while regulating a patient's hematocrit HCT to attain a desired hematocrit value (HCT*), in addition to monitoring the patient's estimated blood volume.

SUMMARY OF THE INVENTION

An apparatus and method is described for rapid venous infusion of physiologic fluid/blood mixtures in a manner that will regulate the hematocrit (HCT) of a patient's blood volume to achieve a pre-set "goal hematocrit" value (HCT*). A dual-pump infusion assembly synchronizes the delivery of fluid and blood through flexible conduits into intravenous (IV) patient catheters. A Blood Replacement Controller (BRC) utilizes measured patient data as feedback input in controlling flowrates of the two infusion pumps to produce the HCT*. The patient's blood volume is extrapolated from hematocrit (HCT) changes in response to the fluid and blood infusion.

The apparatus of the present invention is referred to as the "Blood Infusion Control System (BICS)" and comprises the following components: one or more cannula for infusing a fluid/blood mixture into the venous system of the patient, flexible conduits connecting sources of physiologic fluid/blood into patient cannulas, a two-pump infusion assembly to rapidly propel a physiologic fluid/blood mixture through the conduits, a heat exchanger to control temperature of the infused mixture, a gas vent with filter, sensors to monitor air/pressure/temperature of infused mixture within the fluid conduit, and a blood replacement controller (BRC) to drive the dual-pump infusion assembly. Data used in a computer to control the two infusion pumps is input manually by operator entry with possible inclusion of physiologic information from automatic measurement devices. The said components are available technology in prior art.

The incorporating of the Blood Replacement Controller (BRC) into a design with the above mentioned components, results in an infusion system for regulating patient hematocrit levels and reporting patient blood volumes during rapid fluid resuscitation. Determination of the proper ratio for pump flowrates is quantitatively specified in Equations (7)–(10) set forth below in the Detailed Description. Quantitative relationship of the variables affecting the estimated patient hematocrit ($HCT_E$) are given in Equation (3) set forth below in the Detailed Description. Feedback adjustment of the estimated blood volume ($BV_E$) is given in Equations (13), (25), (28), (29), and (30) set forth below in the Detailed Description.

The apparatus and methodology presented herein represents an innovative device that can provide new ways to administer large quantities of blood, blood components, crystalloid fluids, and colloid fluids. Commercializing the design into a product can provide an apparatus superior to existing blood infusion devices for augmenting the preload of a patient's cardiovascular system during massive transfusions.

The dual-pump design of the present invention provides matched infusion rates of fluid and blood. Proper coupling of these flows through the two pumps will allow regulation of the patient's hematocrit (HCT) to be accomplished. The synchronized two-pump operation of this invention represents a new and useful improvement of prior rapid infusion devices such as the Rapid Infusion System (RIS®) by Haemonetics Corporation of 400 Wood Road, Braintree, Mass. 02184. The present invention offers substantial advantages over conventional systems by regulating a patient's hematocrit and reporting a patient's estimated blood volume.

BRIEF DESCRIPTION OF THE INVENTION

The accompanying drawings, which are incorporated in and constitute a part of the specification, illustrate embodiments of the invention and, together with the detailed description, serve to explain the principles of the invention. These and other features, advantages, operation of the invention will become evident with reference to the drawings in which like reference numerals represent like elements and in which.

DETAILED DESCRIPTION OF THE DRAWINGS

The Blood Infusion Control System (BICS) according to the present invention may have many different embodiments. A preferred embodiment of the BICS, generally referred to be the numeral 1, is disclosed in FIGS. 1 to 11 and is described in detail below.

Figure 1:
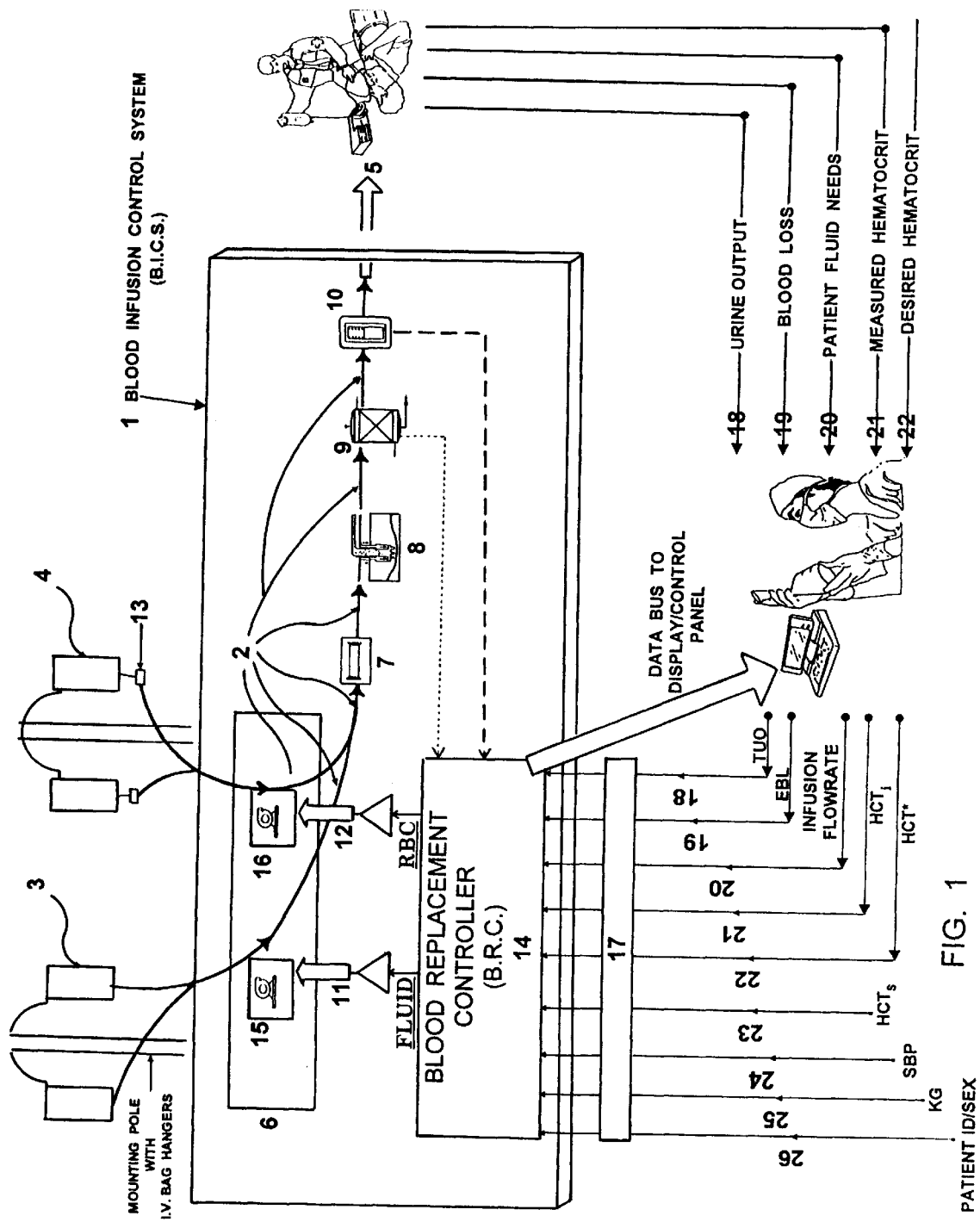
FIG. 1 is a schematic layout that illustrates a preferred embodiment of the Blood Infusion Control System (BICS) of the present invention in which a Blood Replacement Controller (BRC) computes the control signals to actuate the two-pump infusion assembly.

FIG. 1 depicts a schematic representation of the components that comprise the BICS 1. The BICS 1 has flexible tubing 2 acting as a conduit to deliver a source 3 of crystalloid/colloid fluids combined with a source 4 of red blood cells into intravenous patient catheters 5. A two-pump infusion assembly 6 propels the fluid 3 and blood 4 through tubing conduit 2. Modern roller pumps can deliver circulatory supportive fluids at infusion rates from 10 ml per hour for maintenance fluid therapy, up to 3 liters per minute for rapid resuscitation. Before being administered to the patient, the fluid/blood mixture is conditioned by passing through a heat exchanger 7, a gas vent with filter 8, a bubble detector 9, and a pressure/temperature sensor 10. Fluid source 3 and blood source 4 can be in the form of collapsible bags suspended from mounting poles with bag hangers, all of which are commercially available.

A main component of BICS 1 is a Blood Replacement Controller (BRC) 14 that drives the dual-pump infusion assembly 6 via control signal paths 11 and 12. In the preferred embodiment, infusion pump assembly 6 designates infusion pump 15 to propel crystalloid/colloids source 3 and infusion pump 16 to propel blood source 4 through flexible tubing 2. Infusion pumps 15 and 16 are actuated via control signal paths 11 and 12, respectively. The tubing 2 has a high-flow blood filter 13 to allow rapid administration of resuscitation mixtures to the patient.

BRC comprises a microprocessor to compute the coupled flowrates of infusion pumps 15 and 16 based on input information supplied by the operator or by sensors. Patient information that is input into BRC 14 through the data entry port 17 includes:

1) patient ID/sex 26
2) kilogram body weight (KG) 25
3) systolic blood pressure (SBP) 24
4) hematocrit of blood source ($HCT_S$) 23
5) desired patient hematocrit (HCT*) 22
6) measured patient hematocrit ($HCT_i$) 21
7) desired total infusion flowrate (TF) 20
8) estimated blood loss in patient (EBL) 19

9) total urine output in patient (TUO) 18

These inputs can be bused to the BRC 14 in several different known technological forms. Many embodiments can be envisioned using automatic sensors and physiological probes to measure these inputs. Automated sensors are available that can directly input measured data into the BRC 14 through an appropriate interface device 17. In one embodiment, using a keyboard input mode, data is routed to the BRC 14 through a data entry keyboard 17.

In accordance with the invention, the microprocessor controller of BRC 14 drives the infusion pumps 15 and 16 to combine crystalloid/colloid from bags 3 with blood from bags 4 in a selected ratio in order to achieve and maintain HCT*. The methodology used to design the BRC 14 is important to the operation of this rapid infusion control system. The engineering design used to specify the operation of infusion pumps 15 and 16 is set-up to minimize the variational error between $HCT_E$ and HCT*. The formulation of this approach is based on physiologic principles governing changes in plasma volume (PV) and red cell volume (RCV) during blood transfusion.

Physiologic definitions giving the actual percent (% Hct) of a patient's blood volume (BV) that is composed of RCV and PV can be modeled as:

$$BV = PV + RCV \quad \text{EQUATION (1)}$$

$$\% \, Hct/100 = HCT = RCV/BV = RCV/\{PV+RCV\} \quad \text{EQUATION (2)}$$

During fluid resuscitation to stabilize the cardiovascular system of a patient, predictive models for HCT can be expressed using measured values giving: 1) rate of red blood cells added to vascular space via pump 16 at rate of RBC; 2) rate of plasma volume (PV) added to vascular space via pump 15 at rate of FLUID; 3) rate of blood volume lost (BL) from vascular space; 4) rate of urine output (URINE) eliminated from body fluid compartments; 5) patient's kilogram body weight (KG) or body surface area (BSA); and 6) vital signs of systolic blood pressure (SBP).

A variational approach to describe the hemodynamic changes in initial plasma volume ($PV_i$) and initial red cell volume ($RCV_i$) during time interval $\Delta t$ can be represented as:

$$PV_E = PV_i + (\text{ml added to plasma}) - (\text{ml lost from plasma})$$

$$RCV_E = RCV_i + (\text{ml added to red cell mass}) - (\text{ml lost from red cell mass})$$

Changes in the measured hematocrit $HCT_i$ of a patient during $\Delta t$ due to IV infusions, blood loss, and urine output can be expressed as estimated hematocrit values ($HCT_E$) calculated using the working model:
EQUATION (3):

$$HCT_E = \frac{\{HCT_i \times [BV_i - BL \times \Delta t] + HCT_s \times RBC \times \delta t\}}{\{BV_i - BL \times \Delta t + PVE \times \delta t + RBC \times \delta t - .3 \times URINE \times \Delta t\}}$$

In Equation (3):
$HCT_i \times 100 = \%$ hematocrit of patient measured at start time $T_i$
$HCT_s \times 100 = \%$ hematocrit of blood source 4
$\Delta t$=elapsed time since last hematocrit sample at time $T_i$ [$\Delta t$ is given in equation (12)]
$\delta t$=running time that pump assembly 6 operates during $\Delta t$ [$\Delta t$ is given in equation (11)]
$BV_i$=estimated blood volume at initial time $T_i$
FLUID=milliliter per minute (ml/min) flowrate of crystalloid/colloid propelled by infusion pump 15 [FLUID is given in equations (7) and (9)]

PVE=ml/min rate of plasma volume expansion produced by infusion of crystalloids/colloid through 15 at rate given by FLUID [PVE is given in equations (14) and (15)]
RBC=ml/min flowrate of blood propelled through 16 [RBC is given in equations (8) and (10)]

$$TF = RBC + FLUID \quad \text{EQUATION (4)}$$

=total ml/min delivered to patient through tubing 2

$$BL = \Delta EBL/\Delta T \quad \text{EQUATION (5)}$$

=rate of estimated blood loss during time period $\Delta T$ $$URINE = \Delta TUO/\Delta T \quad \text{EQUATION (6)}$$

=rate of urine output during time period $\Delta T$
In response to input patient data 18, 19, 20, 21, 22, 23, 24, and 25, the microprocessor controller of BRC 14 issues command signals 11 and 12 to govern speed adjustment of the two-pump infusion assembly 6 thereby regulating the patient's hematocrit to track HCT*. The BRC 14 utilizes an infusion control law to drive pumps 15 and 16 while delivering a total flowrate TF. This coupled control algorithm specifies the infusion rate of asanguinous fluid through pump 15 and the infusion rate of blood through pump 16. BRC 14 utilizes $HCT_E$ in Equation (3) to track the patient's estimated hematocrit during operation of infusion pumps 15 and 16. $HCT_E$ is derived from physiological principles that governs passage of water, salt, and colloid through body fluid compartments.

Figure 2:
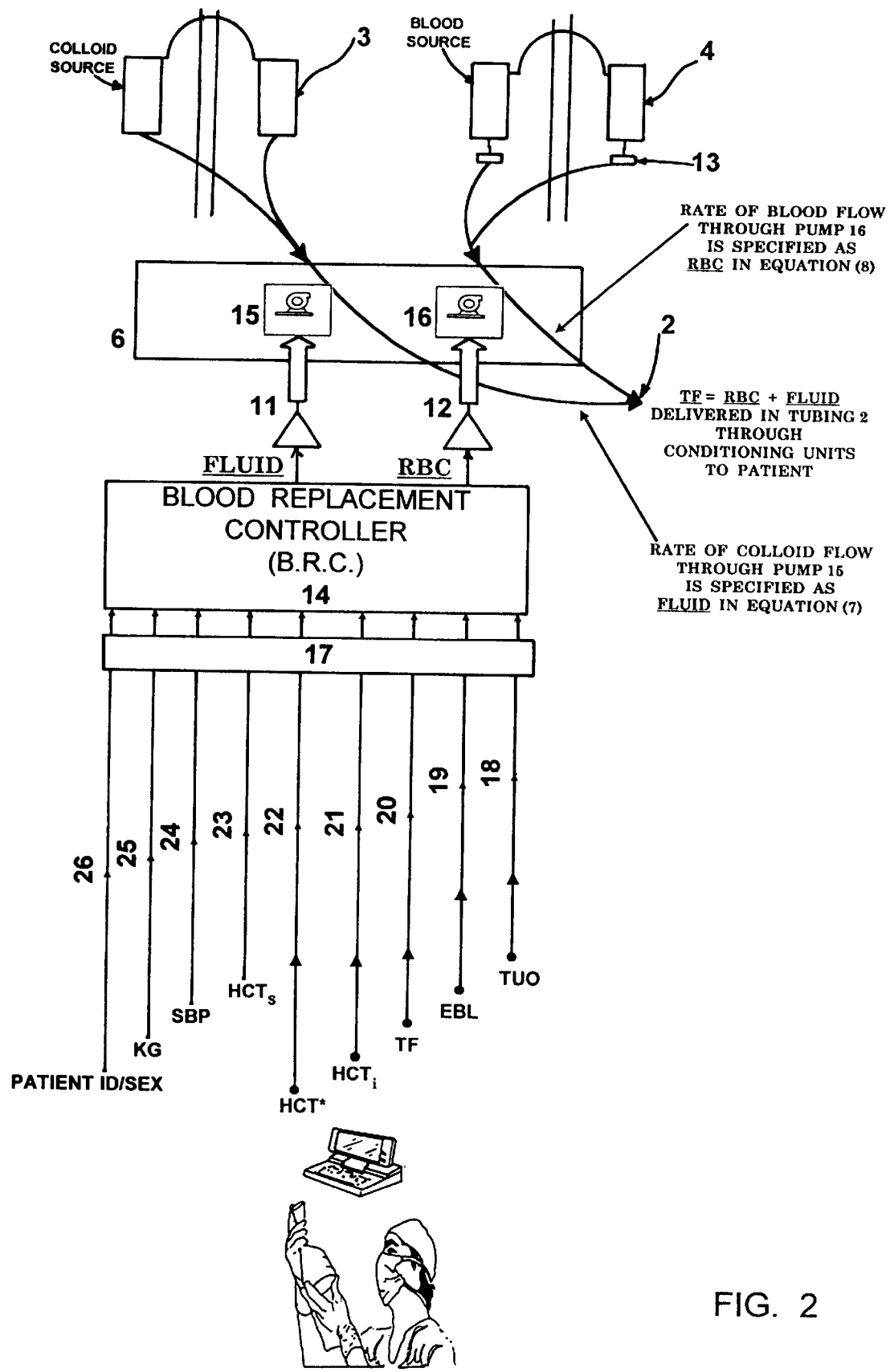
FIG. 2 is a schematic representation of the Blood Replacement Controller (BRC) of the present invention for specifying the coupled flowrates of colloids and blood through the two infusion pumps to produce a desired hematocrit (HCT*) in the patient.

FIG. 2 depicts control signal 11 that actuates infusion pump 15 to propel colloids through tubing 2 at flowrates specified as FLUID. Control signal 12 actuates infusion pump 16 to propel blood through tubing 2 at flowrates specified as RBC. The control law specifies flowrates for colloids infused through pump 15 as:

$$FLUID = TF \times \{HCT_S - HCT^*\}/HCT_S + \{HCT_E - HCT^*\}/HCT_S \times BV_i/\tau + \{HCT_E - HCT^*\}/HCT_S \times BL + 0.3 \times HCT^*/HCT_S \times URINE \quad \text{EQUATION (7)}$$

with the coupled flowrate of blood through 16 as:

$$RBC = TF \times HCT^*/HCT_S - \{HCT_E - HCT^*\}/HCT_S \times BV_i/\tau - \{HCT_E - HCT^*\}/HCT_S \times BL - 0.3 \times HCT^*/HCT_S \times URINE \quad \text{EQUATION (8)}$$

In accordance with the invention, BRC 14 actuates pump 15 to deliver colloids 3 at flowrates based on Equation (7), and actuates pump 16 to deliver a matched flow of the blood source 4 based on Equation (8).

Figure 3:
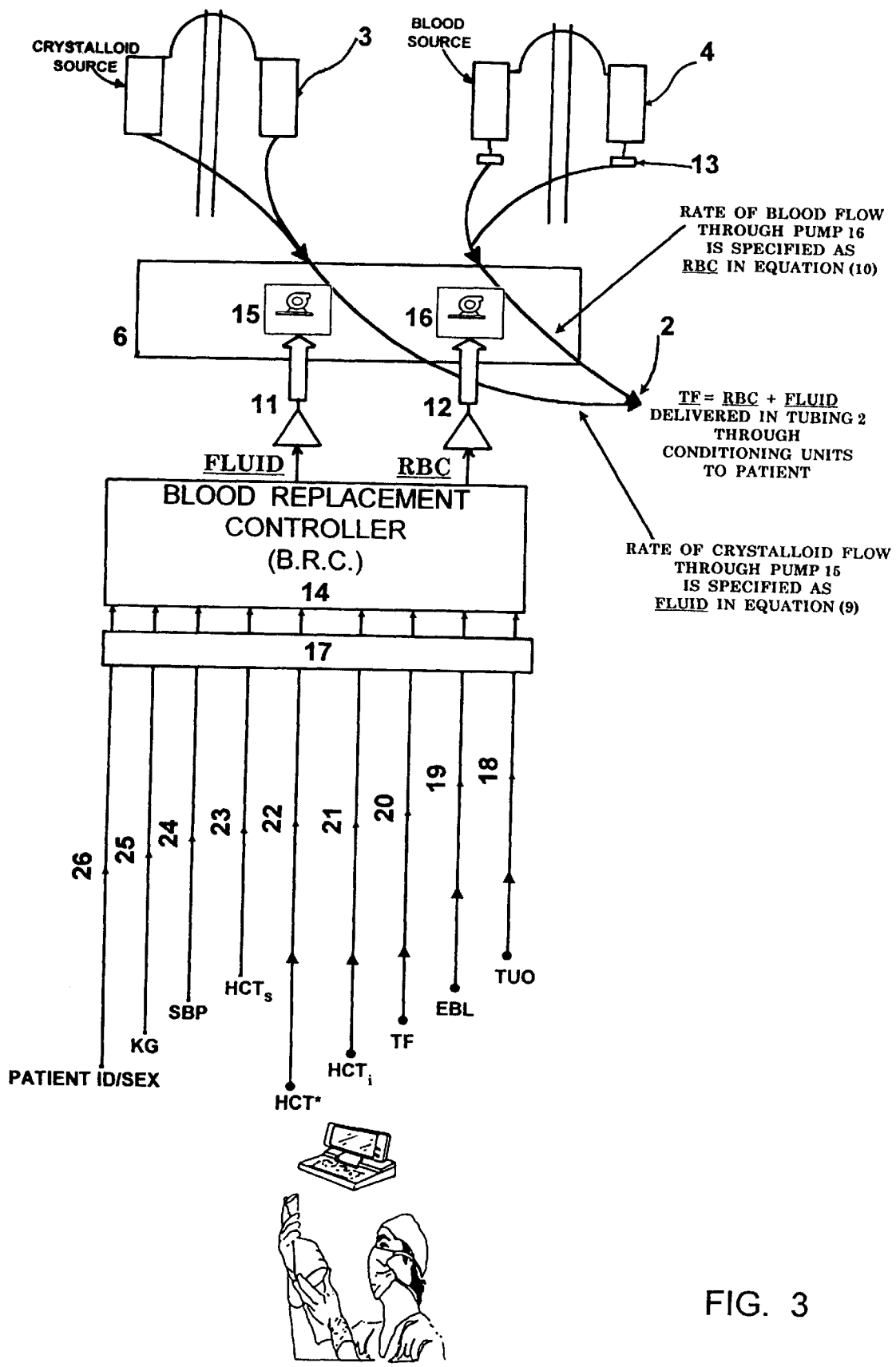
FIG. 3 is a schematic representation of the Blood Replacement Controller (BRC) of the present invention for specifying the coupled flowrates of isotonic crystalloids and blood through the two infusion pumps to produce a desired hematocrit (HCT*) in the patient.

FIG. 3 depicts control signal 11 that actuates infusion pump 15 to propel isotonic crystalloid solutions at flowrates specified as FLUID. Control signal 12 actuates infusion pump 16 to propel blood at flowrates specified as RBC. The control law specifies flowrates of isotonic crystalloids through 15 as:
EQUATION (9)

$$FLUID = TF \times \frac{\{HCT_s - HCT^*\}}{\{HCT_s - .7 \times HCT^*\}} + \frac{\{HCT_E - HCT^*\}}{\{HCT_s - .7 \times HCT^*\}} \times BV_i/\tau + \frac{\{HCT_E - HCT^*\}}{\{HCT_s - .7 \times HCT^*\}} \times BL + \frac{.3 \times HCT^*}{\{HCT_s - .7 \times HCT^*\}} \times URINE$$

with the coupled flowrate for blood infused through 16 as:

EQUATION (10):

$$RBC = TF \times \frac{.3 \times HCT^*}{\{HCT_s - .7 \times HCT^*\}} - \frac{\{HCT_E - HCT^*\}}{\{HCT_s - .7 \times HCT^*\}} \times BV_i / \tau -$$
$$\frac{\{HCT_E - HCT^*\}}{\{HCT_s - .7 \times HCT^*\}} \times BL - \frac{.3 \times HCT^*}{\{HCT_s - .7 \times HCT^*\}} \times URINE$$

In accordance with the invention, BRC 14 actuates pump mechanism 15 to deliver isotonic crystalloids 3 at flowrates based on Equation (9), and actuates pump 16 to deliver a matched flow of the blood source 4 based on Equation (10).

In the control law specified using Equations (7)–(10), $\tau$ represents an infusion time constant related to the rapidity in which a patient's hematocrit changes from $HCT_i$ to $HCT_E$. Values of $\tau$ in the range of 10–20 minutes is an appropriate level.

Figure 4:
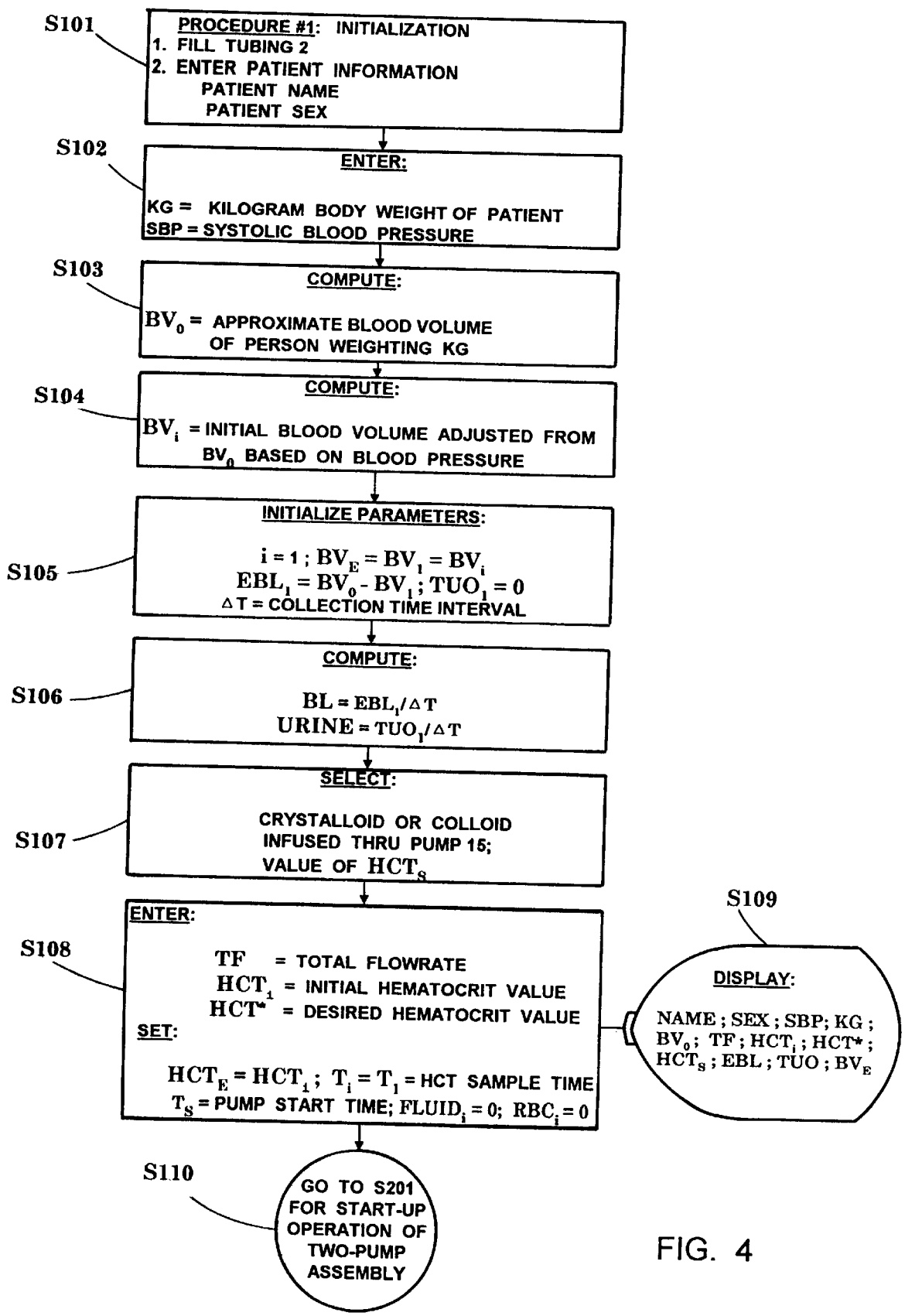
FIG. 4 is a block diagram flowchart of the start-up procedure that initializes the physiologic parameters in the hemodynamic model used to describe changes in the patient's hematocrit (HCT) during fluid and blood infusion by operation of the dual-pump assembly of the present invention.

FIG. 4 depicts a schematic flowchart (PROCEDURE #1) that illustrates (as stated in S101) the initial sequence of instructions to be executed by BRC 14 during start-up operation of BICS 1. The step-by-step instructions are based on guidelines for blood volume determination in trauma patients as established from protocol in the Advanced Trauma Life Support (ATLS) Manual (American College of Surgery, 1993), incorporated herein by reference. In S101, the tubing 2 is filled either manually or with a infusion pump fill procedure. Button D22 in FIG. 11 activates the fill procedure. The operator enters the patient identification and sex 26 into the BRC 14 through keyboard 17. In S102, the patient's kilogram body weight 25 (KG) and systolic blood pressure 24 (SBP) are entered. In S103, the approximate blood volume ($BV_o$) is computed for a normal person with body weight (KG). A preferred embodiment in ATLS Manual gives:

$BV_o$=70×KG for adult males $BV_o$=65×KG for adult females $BV_o$=80×KG for children Many other estimates of $BV_o$ are available using standardized representations with dependent variables such as BSA. In S104, $BV_o$ is adjusted downward to give an initial blood volume based on class of hemorrhage as specified in ATLS Manual. One such embodiment uses a computer model (Lewis, 1986) to give the percent blood volume deficit ($\%\Delta V$) as a function of systolic blood pressure 24 (SBP) measured in the patient:

$\%\Delta V = 50 \times [1-(SBP/120)^{1.6}]^{0.625}$ $BV_i = BV_o \times (100-\%\Delta V)/100$ Other schemes are available to estimate the initial patient blood volume ($BV_i$) in S104. In S105, measurement counter (i) is set to the value of one. Initial values of the estimated blood loss 19 ($EBL_1$) and total urine output 18 ($TUO_1$) are set as:

$EBL_1 = BV_o - BV_i$ $TUO_1 = 0$

Depending on specific clinical situations, the operator may choose to enter initial values for $EBL_1$ and $TUO_1$ that are more appropriate. The collection time interval ($\Delta T$) during which $EBL_1$ and $TUO_1$ occurred is input into BRC 14. If $EBL_1$ or $TUO_1$ are not entered, default values are assumed. In S106, average rates of blood loss and urine output are computed as:

$BL = EBL_1/\Delta T$ $URINE = TUO_1/\Delta T$

In S107, the operator selects the infusion fluid as crystalloid or colloid. The hematocrit value 23 ($HCT_S$) of blood source to be infused through pump 16 is also entered in S107. The initial value of the total flowrate (TF), measured hematocrit ($HCT_i$), and desired hematocrit ($HCT^*$) are entered by the operator in S108. The estimated hematocrit ($HCT_E$) is set equal to the initial measured hematocrit ($HCT_E = HCT_i$). The clock start time is set as the time ($T_i = T_j$) when $HCT_i$ was measured. The pump start time ($T_S$) is set when pump assembly 6 begins to operate. Initial volume of infused fluid ($FLUID_i$) and blood ($RBC_i$) are set to zero (0). In S109, information is shown in the display/control panel (See FIG. 11) that gives patient name, sex, SBP, KG, $BV_o$, TF, $HCT_i$, $HCT^*$, $HCT_S$, EBL, TUO, and $BV_E$. S104–S108 provide data inputs used in Equations (3)–(10) during start-up operation of BRC 14. S110 sends command to S201 (FIG. 5) to begin operation of the two infusion pumps 6.

Figure 5:
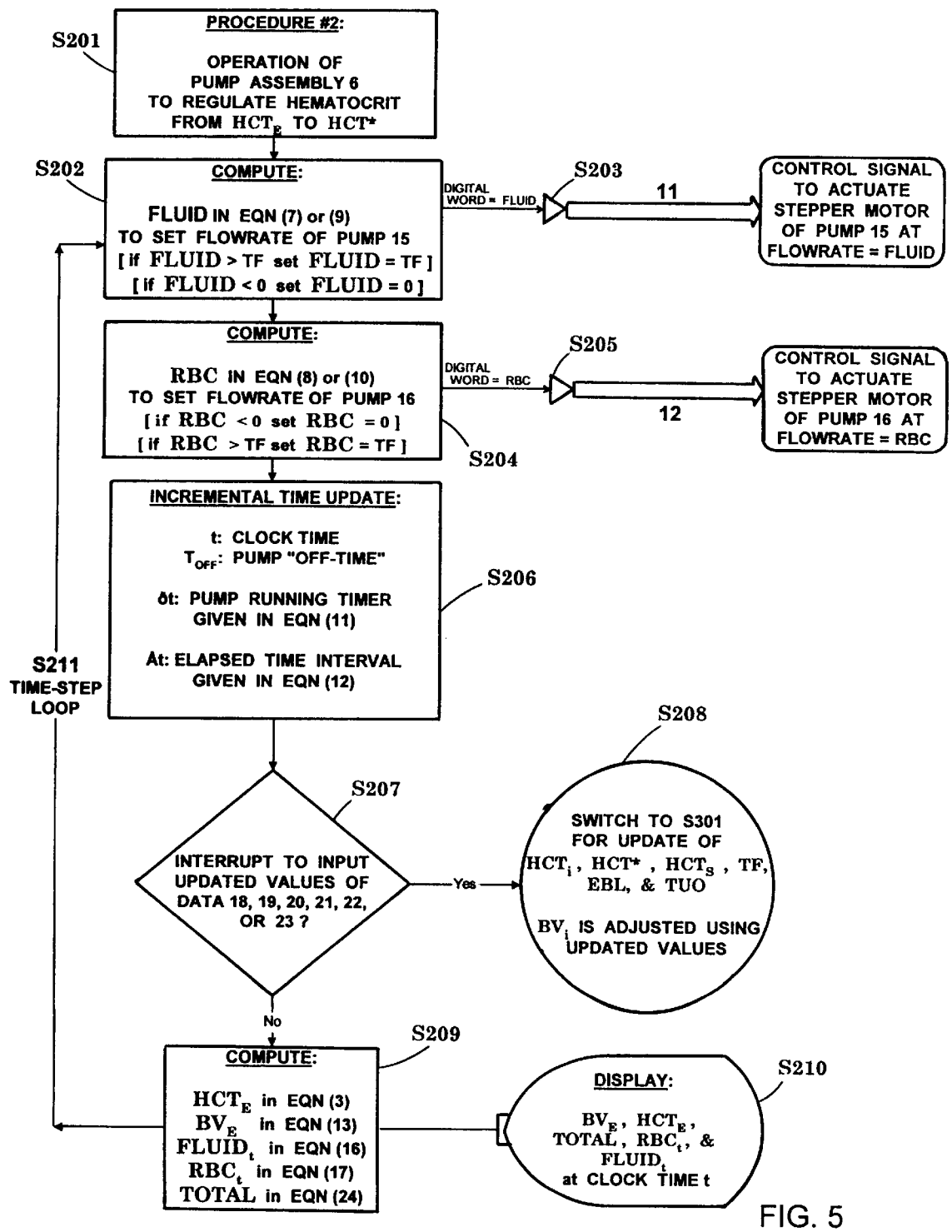
FIG. 5 is a block diagram flowchart of the step-by-step procedure that is executed by the Blood Replacement Controller of the present invention during the process of commanding infusion pump assembly to deliver a balanced fluid/blood mixture that will regulate a patient's hematocrit (HCT) from an initial value $HCT_E$ to a final value HCT*.

FIG. 5 depicts a schematic flowchart (PROCEDURE #2) that illustrates (as stated in S201) the sequence of instructions to be executed by BRC 14 during operation of the BICS 1 to regulate the patient's hematocrit from $HCT_E$ to $HCT^*$. Step-by-step commands are based on calculating the flowrate values from Equations (7)–(10) that control the stepper motor drivers during speed adjustment of dual-pump assembly 6. In a strategy that involves infusing crystalloids through pump 15 at flowrates computed (in S202) as FLUID in Equation (9), while blood is given through pump 16 at flowrates computed (in S204) as RBC in Equation (10). If colloid fluids are infused through pump 15, then FLUID is computed from Equation (7) while RBC is obtained using Equation (8). If FLUID>TF and RBC<0, then set FLUID=TF and RBC=0. If RBC>TF and FLUID<0, then set RBC=TF and FLUID=0.

Infusion pump drivers S203 and S205 apply control signals 11 and 12 to power infusion pumps 15 and 16, respectively. Infusion pump driver S203 converts the digital value FLUID into output voltages (control signal 11) to actuate pump 15 at a flowrate value given by FLUID. Infusion pump driver S205 converts the digital value RBC into output voltages (control signal 12) to actuate pump 16 at a flowrate value given by RBC. S206 is a step that cycles the running time of pumps 15 and 16. This is accomplished by incrementing the clock time denoted as t and the pump assembly "off-time" denoted as $T_{OFF}$. The pump running timer $\delta t$ is given by:

$\delta t = t - T_S - T_{OFF}$   EQUATION (11)

The elapsed time interval $\Delta t$ is given by $\Delta t = t - T_i$   EQUATION (12)

S207 is a branch-point which tests for an interrupt that indicates values of $HCT_i$, $HCT^*$, $HCT_S$, TF, TBL, or TUO are available for input into BRC 14. If a system interrupt is signaled in S207, then S208 invokes a switch to S301 for processing of the input data. The update inputs specified in S301 (FIG. 8) are entered manually by the operator or automatically by data acquisition from sensors for hematocrit and urine output. The estimated blood volume $BV_E$ is then adjusted using updated values of $HCT_i$, BL, URINE, RBC, and FLUID. If a system interrupt is not signaled in S207, then S209 uses the values of $HCT_i$, $HCT_S$, $BV_i$, BL, URINE, FLUID, and RBC in equation (3) to compute estimated values of the patient's hematocrit ($HCT_E$) at clock time t. At this time, the patient's blood volume ($BV_E$) is estimated by:

$$BV_E=BV_i-BL\times\Delta t+PVE\times\delta t+RBC\times\delta t-0.3\times URINE\times\delta t \quad \text{EQUATION (13)}$$

PVE is the rate of plasma volume expansion created by FLUID

PVE=0.3×FLUID if source 3 is isotonic crystalloid      EQUATION (14)

PVE=FLUID if source 3 is colloid      EQUATION (15)

PVE in Equations (14) and (15) represents classic findings of plasma volume expansion involving approximately 30% augmentation by isotonic crystalloids and approximately 100% augmentation by colloids within 30 to 60 minutes. Other variations of BRC 14 that use different plasma volume expansion coefficients are in keeping with this patent.

The total cumulative volume of crystalloid/colloid and blood delivered to the patient at time t is registered in S209 by counter equations:

$$FLUID_t=FLUID_i+FLUID\times\delta t \quad \text{EQUATION (16)}$$

$$RBC_t=RBC_i+RBC\times\delta t \quad \text{EQUATION (17)}$$

Figure 11:
FIG. 11 is a schematic layout of the operator display of the control panel for the BICS of the present invention.

$FLUID_i$ and $RBC_i$ are the cumulative volumes that were infused until time $T_i$ from the fluid source 3 and blood source 4, respectively. The total volume infused (TOTAL) into the patient is given in Equation (24). In S210, display/control panel shown in FIG. 11 gives the updated values of $BV_E$, $HCT_E$, TOTAL, $RBC_t$, and $FLUID_t$ at clock time t. After an incremental time-step loop in S211, FLUID and RBC are re-computed in S202 and S204 using Equations (7)–(10) with estimated parameters that were updated in S209.

Using FLUID and RBC as the digital flowrate values delivered to a 100 kg patient, time profiles of the hematocrit response are graphically represented in FIGS. 6A-B and 7A-B.

Figure 6A:
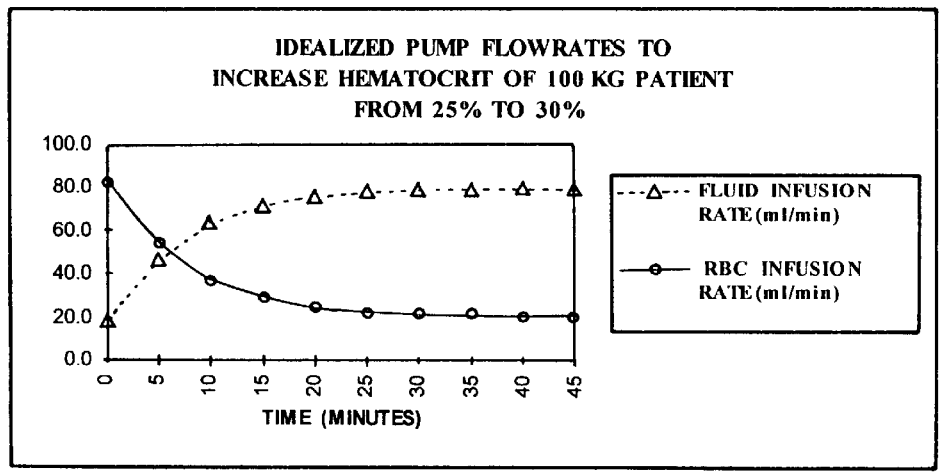
FIGS. 6A and 6B are idealized time profile graphs of the blood infusion rate, the fluid infusion rate, and the resulting hematocrit change which occur as the Blood Replacement Controller (BRC) of the present invention elevates a patient's hematocrit from $HCT_E=25\%$ to $HCT^*=30\%$.
Figure 6B:
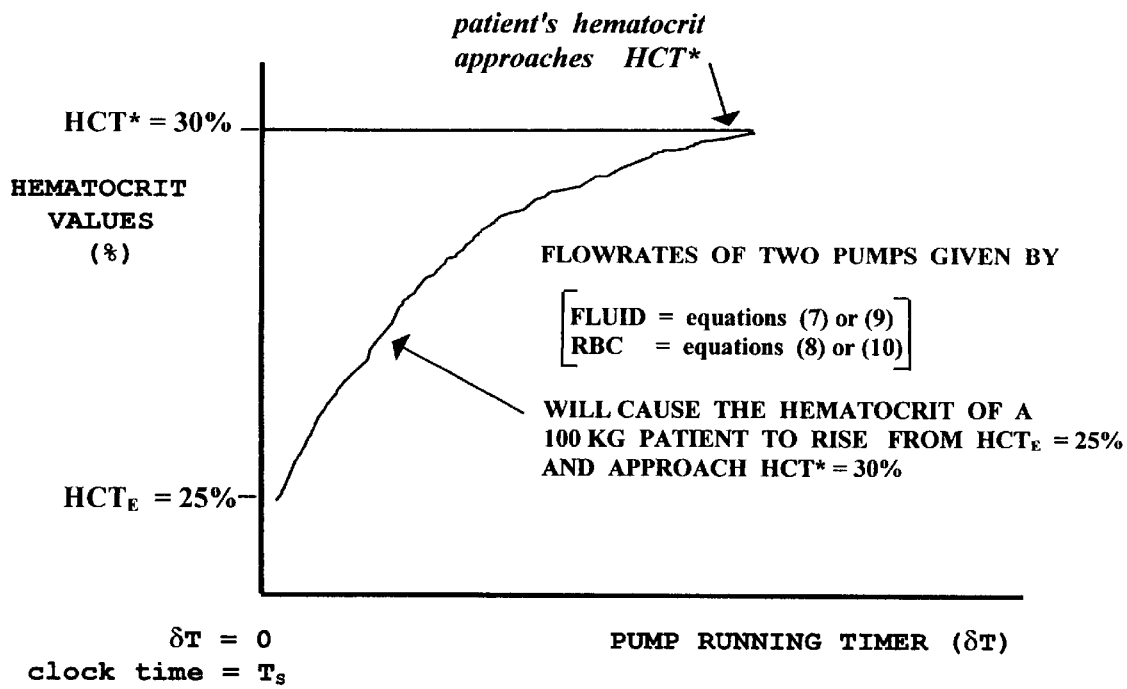

FIGS. 6A and 6B depict the time profiles that occur when BICS 1 elevates a patient's hematocrit from a value of $HCT_E$=25% to the desired value of HCT*=30%. The commands issued to pump assembly 6 are FLUID (equation (7) or (9)) and RBC (equation (8) or (10)). Beginning at clock start time $T_S$ (defined as running time δt=0), the synchronized flowrates shown will regulate HCT to approach 30%. In this example, total flowrate delivered is: TF=FLUID+RBC=100 ml/min.

Figure 7A:
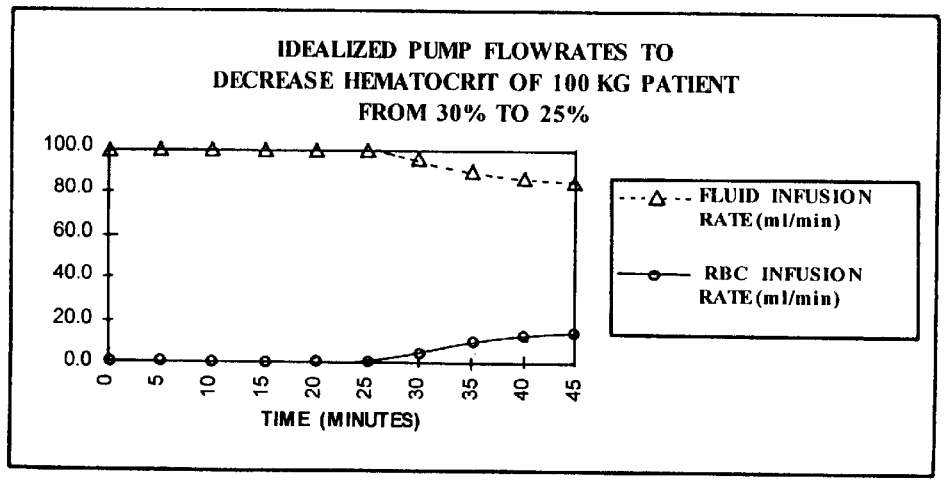
FIGS. 7A and 7B are idealized time profile graphs of the blood infusion rate, the fluid infusion rate, and the resulting hematocrit changes which occur as the Blood Replacement Controller (BRC) of the present invention lowers a patient's hematocrit from $HCT_E=30\%$ to $HCT^*=25\%$.
Figure 7B:
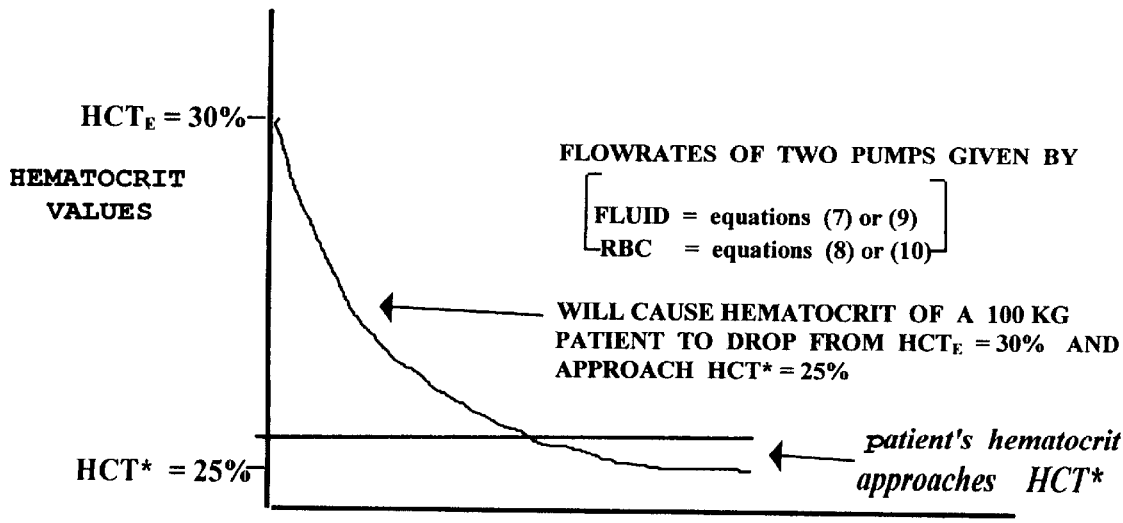

FIGS. 7A and 7B depict the time profiles that occur when BICS 1 lowers a patient's hematocrit from an initial value of $HCT_E$=30% to the desired value of HCT*=25%. The commands issued to pump assembly 6 are FLUID [equation (7) or (9)] and RBC [equation (8) or (10)]. Beginning at clock start time $T_S$ (defined as running time δt=0), the synchronized flowrates shown will regulate HCT to approach 25%. In this example, total flowrate delivered is: TF=FLUID+RBC=100 ml/min.

Figure 8:
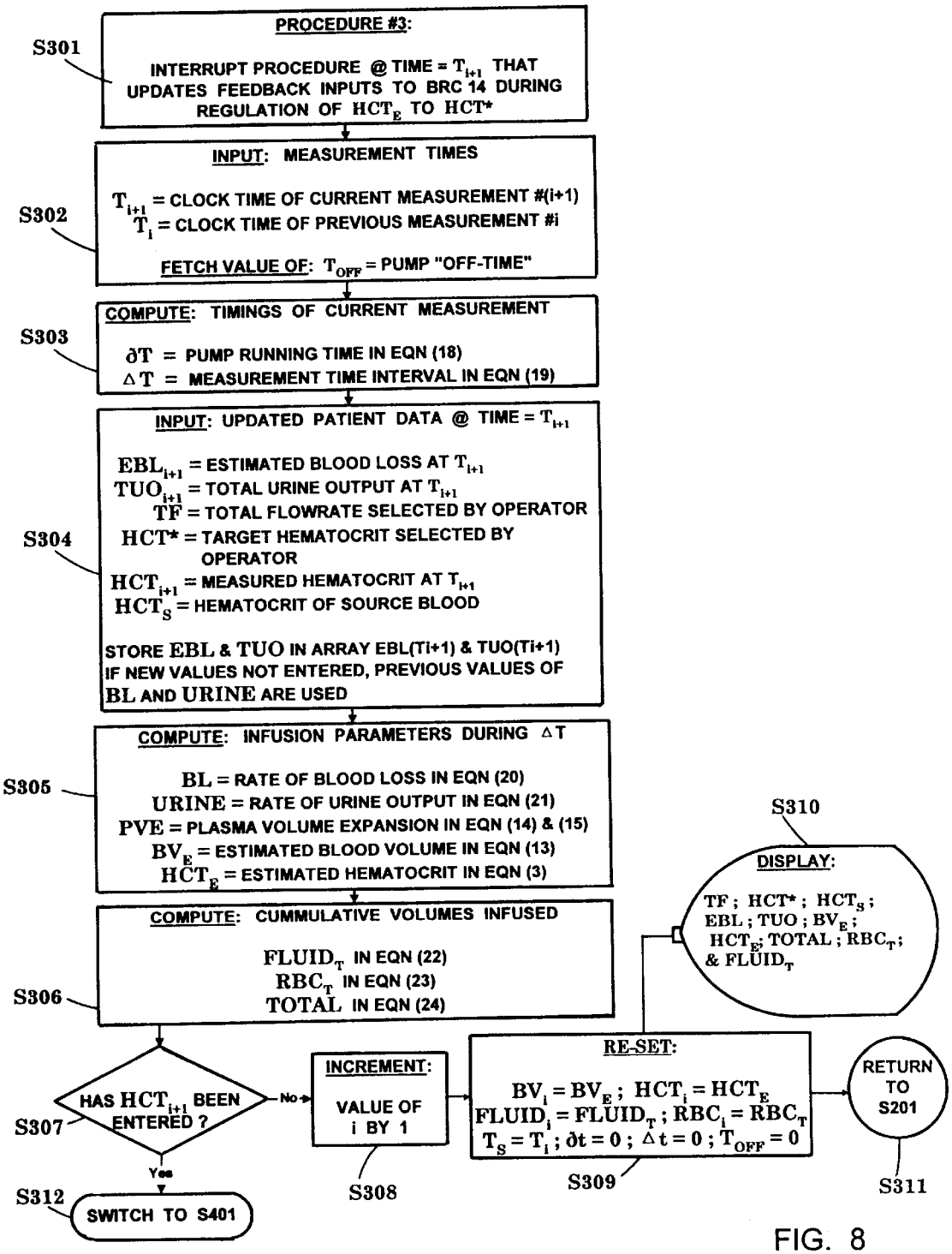
FIG. 8 is a block diagram flowchart of the step-by-step procedure in which measured hemodynamic data is used as feedback input in 1) the working model for estimating the patient's hematocrit ($HCT_E$) and 2) the control law for determining flowrates of the two infusion pumps of the apparatus of the present invention.

FIG. 8 depicts a schematic flowchart (PROCEDURE #3) that illustrates (as stated in S301) the sequence of instructions to update feedback parameters in the control law employed by BRC 14 during regulation of the patient's hematocrit from $HCT_E$ to HCT*. The input of measured parameters provided by automatic sensors or the operator will cause a change in the infusion of fluids and blood through pump assembly 6 by recalculating the control law given in Equations (7)–(10). In S302, the measurement time is set equal to clock time $T_{i+1}$ when the updated parameters were recorded. $T_i$ is the clock time recorded for the previously measured sample. The value of pump "off-time" ($T_{OFF}$) is retrieved as the elapsed time that pump assembly 6 was idle in the "halt mode". Pump assembly 6 may need to be placed in the "halt mode" for reasons such as automatic shutdown due to air detection in tubing 2 or manual shutdown to correct problems with intravenous patient catheter 5, etc. Timings of current interval are computed in S303 as:

$$\delta T=T_{i+1}-T_i-T_{OFF}=\text{pump running time} \quad \text{EQUATION (18)}$$

$$\Delta T=T_{i+1}-T_i=\text{measurement time interval} \quad \text{EQUATION (19)}$$

In S304, the operator or automatic sensors enter the new patient data that was measured at time $T_{i+1}$. The updated data includes any or all of the following:

$EBL_{i+1}$=estimated blood loss from patient at time $T_{i+1}$ $TUO_{i+1}$=total urine output produced by patient at time $T_{i+1}$ TF=total flowrate selected by operator HCT*=target hematocrit selected by operator $HCT_{i+1}$=patient hematocrit measured at $T_{i+1}$ $HCT_S$=hematocrit of source blood In S305, the infusion parameters are computed as:

ΔT=measurement time interval given in Equation (19)
EQUATION (20):

$$BL = \frac{EBL_{i+1} - EBL_i}{\Delta T}$$

EQUATION (21):

$$URINE = \frac{TUO_{i+1} - TUO_i}{\Delta T}$$

PVE is the plasma volume expansion specified as:

PVE=0.3×FLUID if source 3 is isotonic crystalloid (See Equation 14)

PVE=FLUID if source 3 is colloid (See Equation 15)

$BV_E$=estimated blood volume given in Equation (13)

$HCT_E$=estimated hematocrit given in Equation (3)

In S306, the total volumes infused are computed as:

$$FLUID_T=FLUID_i+FLUID\times\delta T \quad \text{EQUATION (22)}$$

where $FLUID_T$=total volume of fluid infused from source 3

$FLUID_i$=cumulative volume infused from fluid source 3 until time $T_i$ and

FLUID×δT=additive volume infused from fluid source 3 during time interval ΔT.

$$RBC_T=RBC_i+RBC\times\delta T \quad \text{EQUATION (23)}$$

where $RBC_T$=total volume of blood infused from source 4

$RBC_i$=cumulative volume infused from blood source 4 until time $T_i$ and

RBC×δT=additive volume infused from blood source 4 during time interval ΔT.

Total volume delivered to the patient through tubing 2 from fluid source 3 and blood source 4 is computed by:

$$TOTAL=FLUID_T+RBC_T \quad \text{EQUATION (24)}$$

In S307, a switching decision is made based on whether or not a new hematocrit value ($HCT_{i+1}$) has been entered. If a new value $HCT_{i+1}$ has not been entered in S304, then S308 increments the measurement counter (i) by one in preparation for the next set of measurement inputs. In S309, parameters of the working models for $HCT_E$ and $BV_E$ are re-set. Blood volume ($BV_i$) at time $T_i$ is set equal to the value calculated for $BV_E$. Hematocrit value ($HCT_i$) at time $T_i$ is set equal to the value calculated for $HCT_E$. The initial volume of fluid from source 3 ($FLUID_i$) and blood from source 4 ($RBC_i$) at time $T_i$ are set equal to the computed values of $FLUID_T$ and $RBC_T$. Timer values are re-set to $T_S = T_i$, $\delta t = 0$, $\Delta t = 0$ and $T_{OFF} = 0$. In S310, display/control panel shown in FIG. 11 gives the updated values of TF, $HCT^*$, $HCT_S$, EBL, TUO, $BV_E$, $HCT_E$, TOTAL, $RBC_T$, and $FLUID_T$. In S311, the command control is returned to S201 in order to operate pump assembly 6 using new infusion parameters that were updated in S305 and S306. If a new value $HCT_{i+1}$ has been entered in S304, then S312 switches program control to S401 in order to make adjustments to $BV_{E \text{ using } HCTi+1}$.

Figure 9:
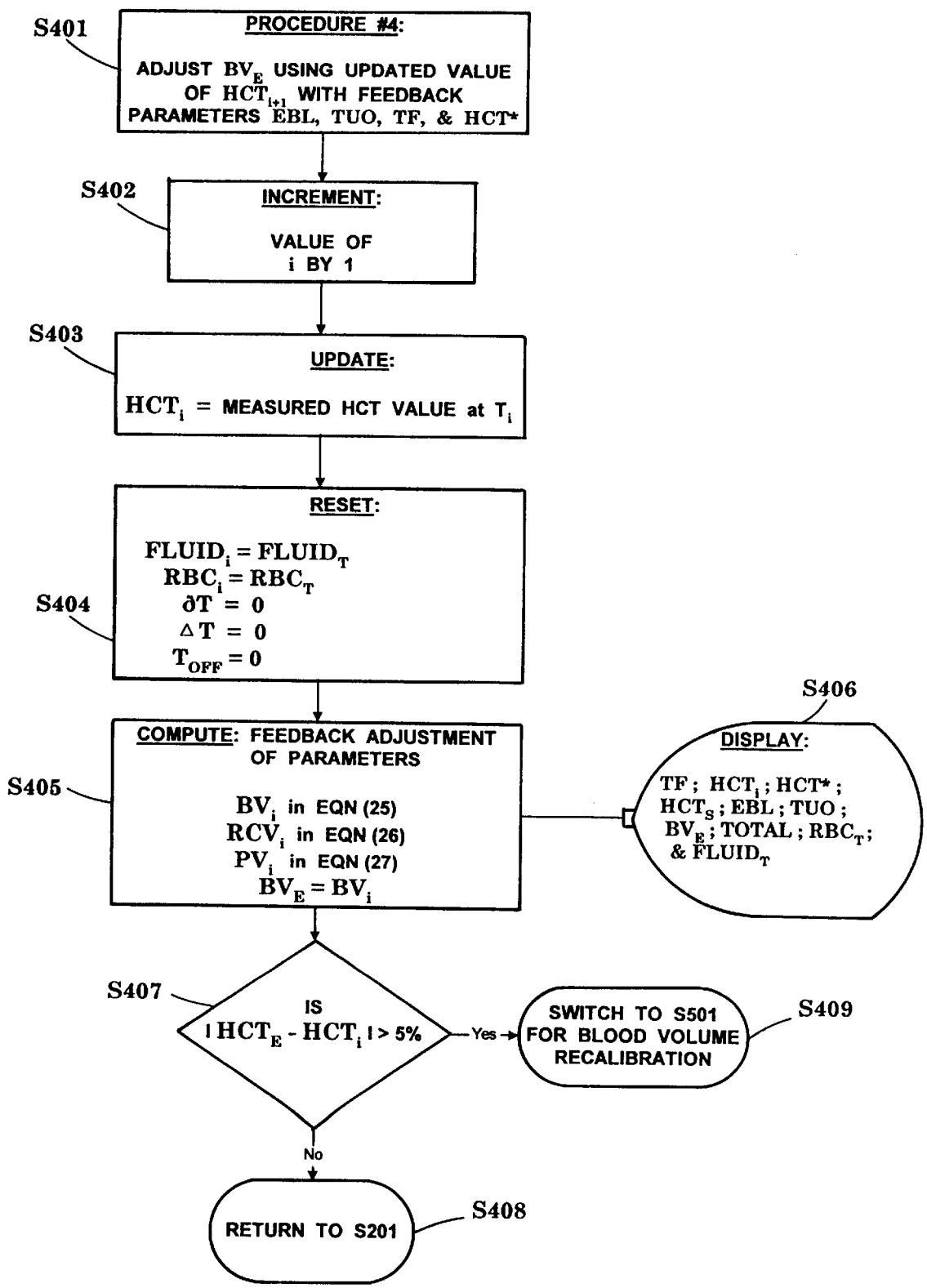
FIG. 9 is a block diagram flowchart of the step-by-step procedure in which measured hematocrit values are used to adjust the estimated blood volume ($BV_E$) that is incorporated as feedback input in 1) the working model for estimating the patient's hematocrit ($HCT_E$), and 2) the control law for determining flowrates of the two infusion pumps of the present invention.

FIG. 9 depicts a schematic flowchart (PROCEDURE #4) that illustrates (as stated in S401) instructions to adjust the estimated blood volume ($BV_E$) using updates of the measured hematocrit values. In S402, measurement counter (i) is incremented by one (1). In S403, $HCT_i$ is updated to be the measured hematocrit value at time $T_i$. The updated hematocrit value was measured in S304 by laboratory methods from blood samples or by automatic sensors. In S404, the initial volumes of fluid from source 3 ($FLUID_i$) and blood from source 4 ($RBC_i$) are set equal to the values of $FLUID_T$ and $RBC_T$ as reported in S306. Timer values are reset to $T_S = T_i$, $\delta t = 0$, $\Delta T = 0$, and $T_{OFF} = 0$. In S405, feedback adjustment of blood volume is accomplished using:

$$BV_i = BV_E + (HCT_i - HCT_E) \times BV_E \quad \text{EQUATION (25)}$$

Several formulations of the updated blood volume are possible in keeping with the scope of this patent. The approximate red cell volume ($RCV_i$) and plasma volume ($PV_i$) of the patient at $T_i$ is then given by:

$$RCV_i = HCT_i \times BV_i \quad \text{EQUATION (26)}$$

$$PV_i = (1 - HCT_i) \times BV_i \quad \text{EQUATION (27)}$$

The estimated blood volume ($BV_E$) for the next time step is now set equal to the feedback adjusted blood volume ($BV_i$). In S406, the display/control panel shown in FIG. 11 gives updated values of TF, $HCT_i$, $HCT^*$, $HCT_S$, EBL, TUO, $BV_E$, TOTAL, $RBC_T$, and $FLUID_T$. In S407, a check is made to determine if the measured value of $HCT_i$ differs from the calculated value of $HCT_E$ by more than 5%. The 5% error tolerance is an arbitrary value that can be modified. If $HCT_E$ differs from $HCT_i$ by less than 5%, S408 returns program control to S201 in order to operate pump assembly 6 during the next time step using the new infusion parameters updated in S405, S304, and S305. If $HCT_E$ differs from $HCT_i$ by more than 5%, S409 switches program control to S501 for a physiologic re-calibration of the blood volume $BV_i$.

Figure 10:
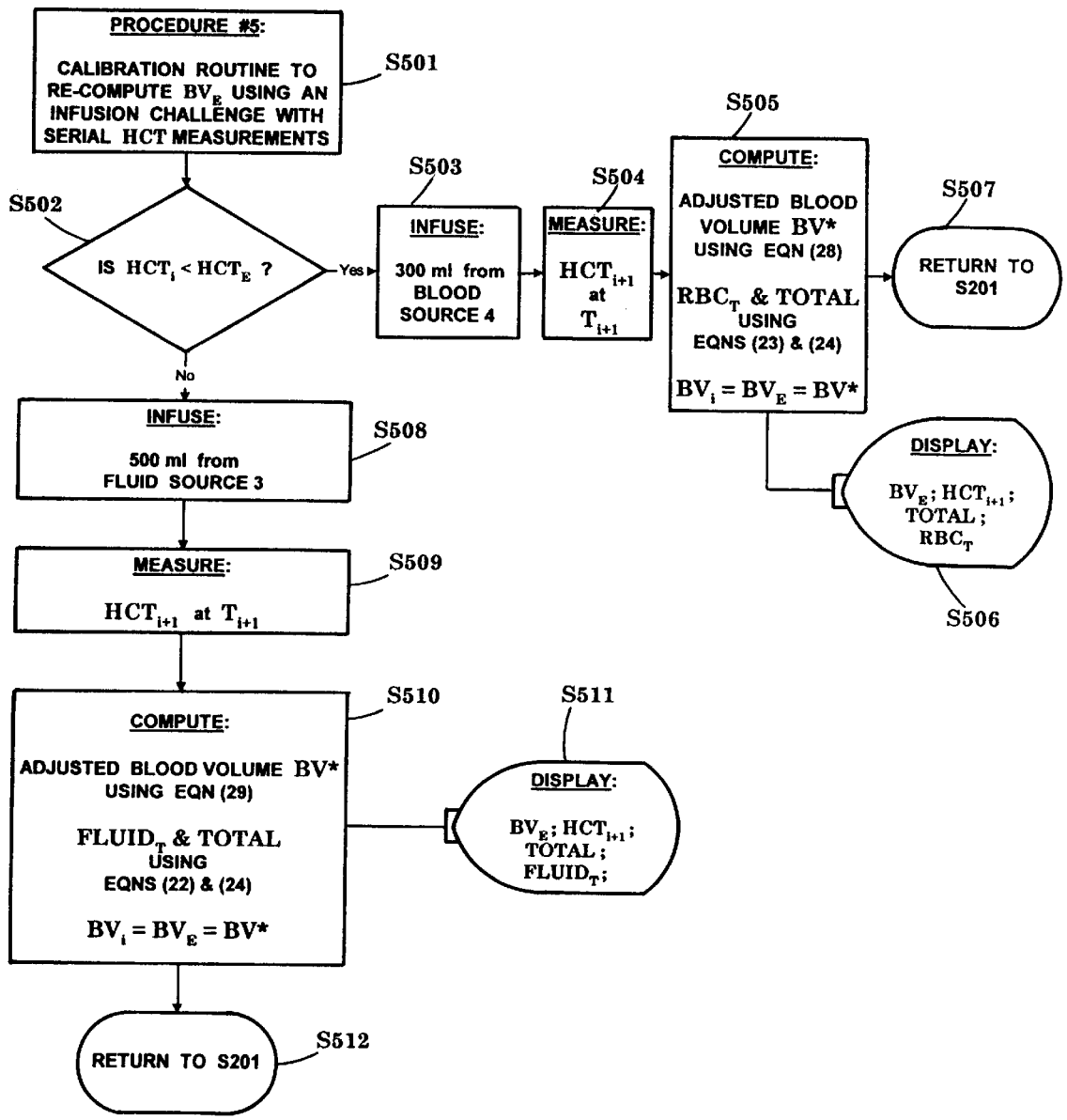
FIG. 10 is a block diagram flowchart of the step-by-step procedure of the present invention in which the estimated blood volume ($BV_E$) is recalibrated by employing a rapid injection of fluid or blood depending if the measured hematocrit ($HCT_i$) is too high or too low when compared with $HCT_E$.

FIG. 10 depicts a schematic flowchart (PROCEDURE #5) that illustrates (as stated in S501) the sequence of instructions for a physiologic re-calibration of blood volume $BV_i$. This routine uses an infusion challenge with serial measurements of hematocrit values to re-compute $BV_i$. In S502, a check is made to determine if $HCT_i$ is less than $HCT_E$.

If $HCT_i < HCT_E$, then S503 specifies a 300 ml infusion from blood source 4. The 300 ml is the approximate volume in one unit of packed red blood cells. This suggested 300 ml volume for the blood challenge can be modified without departing from the scope of the present invention. After the blood challenge, a new hematocrit $HCT_{i+1}$ is measured at time $T_{i+1}$ in S504. In S505, the time duration of the blood challenge is defined as $\Delta T = T_{i+1} - T_i$. The adjusted blood volume $BV^*$ is then computed by:

$$BV^* = (BV_i - BL \times \Delta T) \times HCT_i / HCT_{i+1} + 300 \times HCT_S / HCT_{i+1} + BL \times \Delta T - 300 \quad \text{EQUATION (28)}$$

The new estimated blood volume ($BV_E = BV_{i+1}$) at time $T_{i+1}$ is then set equal to the computed value of $BV^*$. The 300 ml is tallied into accumulated sums for $RBC_T$ and TOTAL using Equations (23) and (24). The value of the measurement counter (i) is increased by one in preparation for the next set of measurement inputs. In S506, updated values of $BV_E$, $HCT_i$, TOTAL, and $RBC_T$, are presented in the display/control panel in FIG. 11. In S507, command control is returned to S201 in order to operate pump assembly 6 during the next time step using the new infusion parameters updated in S504, S505, S304, and S305.

If $HCT_i > HCT_E$, then S508 specifies a 500 ml infusion of isotonic crystalloid from fluid source 3. This suggested 500 ml volume for the fluid challenge is an arbitrary value that can be modified without departing from the scope of the present invention. After the fluid challenge, a new hematocrit $HCT_{i+1}$ is measured at time $T_{1+1}$ in S509. In S510, the time duration of the fluid challenge is defined as $\Delta T = T_{i+1} - T_i$. The adjusted blood volume $BV^*$ is then computed by:

$$BV^* = (BV_i - BL \times \Delta T) \times HCT_i / HCT_{i+1} + BL \times \Delta T - 150 \quad \text{EQUATION (29)}$$

If 300 ml of a colloid is used in the fluid challenge then by:

$$BV^* = (BV_i - BL \times \Delta T) \times HCT_i / HCT_{i+1} + BL \times \Delta T - 300 \quad \text{EQUATION (30)}$$

The new estimated blood volume ($BV_E = BV_{i+1}$) at time $T_{i+1}$ is then set equal to the computed value of $BV^*$. The volume of the fluid challenge is tallied into accumulated sums for $FLUID_T$ and TOTAL using equations (22) and (24). The value of the measurement counter (i) is increased by one in preparation for the next set of measurement inputs. In S511, updated values of $BV_E$, $HCT_i$, TOTAL, and $FLUID_T$ are presented in the display/control panel in FIG. 11. In S512, command control is returned to S201 in order to operate pump assembly 6 during the next time step using the new infusion parameters updated in S509, S510, S304, and S305.

FIG. 11 depicts a stylized layout representing the display/control panel used by the operator when giving transfusion therapy with BICS 1. Data is entered into the BRC 14 by operator input via alphanumeric keyboard or by automatic sensors via data channels. The entered data and calculated parameters are displayed in the graphics panel. This display/control panel is divided into five sections: 1) Patient Information 2) Control Setting Inputs 3) Patient Physiological Parameters 4) Infusion Totals 5) Pump Controls.

In the Patient Information section, D1 is the patient name which was entered in S101 by the operator via the keyboard. D2 is the sex of the patient which was entered in S101 by the operator. D3 is the systolic blood pressure which was entered in S102. D4 is the clock time which is generated by the microcomputer. D5 is the kilogram body weight of the patient which was entered in S102. D6 is the approximate blood volume of a normal patient which was computed in S103.

In the Control Setting Inputs section, D7 is the total flowrate (TF) which was set by the operator in S108 and S304. D8 is the measured hematocrit ($HCT_i$) which was input in S108, S304, S403, S504, and S509. D9 is the target hematocrit ($HCT^*$) which was entered by the operator in S108 and S304. D10 is the hematocrit of the blood source ($HCT_S$) which was entered in S108 and S304. D11 is the estimated blood loss (EBL) which was specified in S105 and S304. D12 total urine output (TUO) which was entered in S105 and S304. D13 is the fluid type (crystalloid or colloid) which was initially entered in S107 and can be changed with a system interrupt.

In the Patient Physiological Parameters section, D14 is the estimated blood volume ($BV_E$) of the patient which was computed in S104, S209, S305, S405, S505, and S510. D15 is a graph displaying the time profile of $BV_E$. D16 is the patient's estimated hematocrit ($HCT_E$) which was computed in S209 and S305.

In the Infusion Totals section, D17 is the infusion pump running time which was determined in S206 and re-set in S404. D18 is total infused volume (TOTAL) which was tallied in S209, S306, S505, and S510. D19 is the total infused blood volume ($RBC_T$) which was counted in S209, S306, and S505. D20 is the total infused crystalloid volume ($FLUID_T$) which was counted in S209, S306, and S510. D21 is the total infused colloid volume ($FLUID_T$) which was tallied in S209, S306, and S510.

In the Pump Controls section, D22 is a push-button switch to initiate automatic filling of tubing 2 after the disposable tubing 2 has been loaded into the BICS D23 is a push-button switch to initiate operation of infusion pump assembly 6 using information specified in the Control Setting Input section. D24 is a push-button switch to immediately stop operation of the infusion pump assembly 6. D25 is a push-button switch to initiate the re-calibration procedure specified in S501.

Other alterations and modifications of the invention will likewise become apparent to those of ordinary skill in the art upon reading the present disclosure. It is intended that the scope of the invention disclosed herein be limited only by the broadest interpretation of the appended claims to which the inventor is legally entitled.

What is claimed is:

1. A blood infusion control system for venous infusion of physiologic fluid for achieving pre-set hematocrit levels in a patient and reporting the patient's blood volume during administration of transfusion therapy, said system comprising:
    an infusion assembly having a first infusion pump for propelling a first physiologic fluid into the body of a patient and a second infusion pump for propelling a second physiologic fluid into the body of the patient, said first and second infusion pumps having variable flowrates and operating in sychronized relationship to each other; and
    a controller for controlling the operation of said first and second infusion pumps to regulate the flowrates of said first and second physiologic fluids being propelled by said first and second infusion pumps, said controller synchronizing the flowrate of said first and second infusion pumps to control the total flowrate of said first and second infusion pumps in response to a patient's hematocrit levels and blood volume.

2. The system of claim 1 in which said first physiologic fluid is blood.

3. The system of claim 1 in which said second physiologic fluid includes crystalloid/colloid fluids.

4. The system of claim 1 further comprising a heat exchanger for controlling the temperature of said first and second physiologic fluids.

5. The system of claim 1 further comprising a gas vent.

6. The system of claim 1 further comprising sensors for monitoring properties of said first and second physiologic fluids.

7. The system of claim 1 further comprising means for inputting patient data into said controller.

8. The system of claim 1 further comprising an in-line conditioning unit for creating a warmed, bubble-free stream of first and second physiologic fluid mixture for delivery into intravenous patient catheters.

9. The system of claim 1 further comprising at least one cannula for infusing a first and second physiologic fluid mixture into the venous system of the patient.

10. The system of claim 1 further comprising means for measuring patient data and inputting said data into said controller.

11. The system of claim 1 further comprising means for estimating blood volume from hematocrit changes in a patient in response to infusion of said first and second physiologic fluids.

12. A system for administering transfusion therapy to a patient, comprising a computer processor programmed to control the conjoined cyclical motion of first and second infusion pumps operating at variable flowrate ratios in combination with elements to condition physiologic fluids and blood to be acceptable for delivery through flexible tubing into patient catheters.

13. The system of claim 12 further comprising:
    (a) said first infusion pump propelling physiologic fluids through said tubing and said second infusion pump propelling blood through said tubing;
    (b) a controller that uses variational algorithms to specify the conjoined cyclical motion of said first and second infusion pumps that produce said variable flowrate ratios of said physiologic fluids and blood delivered through said tubing; and
    (c) elements to produce warm physiologic fluids and blood which is devoid of air before being delivered through said tubing.

14. The system of claim 12 wherein said first infusion pump delivers physiologic fluids, which includes crystalloid solutions and colloid suspensions and said second infusion pump delivers various forms of blood.

15. The system of claim 13 wherein said first and second infusion pumps operate at variable flowrate ratios, in relation to each other, as commanded by said controller.

16. The system of claim 13 wherein said first and second infusion pumps vary infusion rates in response to programmable variables that are input into said controller.

17. The system of claim 13 wherein said controller drives said first and second infusion pumps by determining metered flowrates for coupled administration of the physiologic fluids and blood that achieves pre-selected hematocrit levels in a patient according to inputs provided by an operator.

18. The system of claim 13 wherein said controller drives said first and second infusion pumps by determining metered flowrates for coupled administration of the physiologic fluids and blood that achieves pre-selected hematocrit levels in a patient according to inputs provided by an operator with inclusion of inputs from automatic sensors.

19. The system of claim 12 further comprising:
    (a) an inline heat exchanger element to control temperatures of the infused physiologic fluids and blood;
    (b) an inline evacuation element to remove air from the infused physiologic fluids and blood;
    (c) inline elements to sense hydrostatic parameters within the flexible tubing and hemodynamic parameters within the patient; and
    (d) elements to warn an operator or to automatically shut off said system when unacceptable conditions exist in the physiologic fluids and blood delivered to the patient.

20. A method for specifying variable flowrate ratios of infusion pumps comprising the steps of:
    (a) providing a computer processor programmed to control the conjoined cyclical motion of first and second infusion pumps operating at variable flowrate ratios in combination with elements to condition physiologic fluids and blood to be acceptable for delivery through flexible tubing into patient catheters;

(b) achieving a variable total flowrate, as set by an operator, of said physiologic fluids and blood;

(c) regulating said patient's hematocrit level to achieve a value pre-selected by the operator; and (d) reporting an estimate of the patient's blood volume and other related hemodynamic parameters whereby the operator can simultaneously infuse the physiologic fluids and blood into the patient without having to pre-mix these components in a mixing chamber before delivery through a single pump.

* * * * *